(12) United States Patent
Bauer et al.

(10) Patent No.: US 8,825,180 B2
(45) Date of Patent: Sep. 2, 2014

(54) MEDICAL ELECTRICAL LEAD WITH CO-RADIAL MULTI-CONDUCTOR COIL

(75) Inventors: Ryan T. Bauer, Brooklyn Park, MN (US); John L. Sommer, Coon Rapids, MN (US)

(73) Assignee: Medtronic, Inc., Minneapolis, MN (US)

(*) Notice: Subject to any disclaimer, the term of this patent is extended or adjusted under 35 U.S.C. 154(b) by 1276 days.

(21) Appl. No.: 11/095,192

(22) Filed: Mar. 31, 2005

(65) Prior Publication Data

US 2006/0229693 A1    Oct. 12, 2006

(51) Int. Cl.
*A61N 1/37* (2006.01)
*A61N 1/05* (2006.01)
*A61N 1/375* (2006.01)
*A61N 1/08* (2006.01)

(52) U.S. Cl.
CPC .. *A61N 1/05* (2013.01); *A61N 1/37* (2013.01); *A61N 1/3752* (2013.01); *A61N 2001/086* (2013.01)
USPC ............................ 607/121; 607/116; 607/119

(58) Field of Classification Search
CPC ......... A61N 1/05; A61N 1/3752; A61N 1/37; A61N 2001/086
USPC .................................. 607/116, 119, 121, 122
See application file for complete search history.

(56) References Cited

U.S. PATENT DOCUMENTS

| | | | |
|---|---|---|---|
| 4,280,511 A | | 7/1981 | O'Neill |
| 5,065,769 A | * | 11/1991 | de Toledo .................... 600/585 |
| 5,629,622 A | | 5/1997 | Scampini |
| 5,897,584 A | * | 4/1999 | Herman ........................ 607/122 |
| 5,964,705 A | | 10/1999 | Truwit et al. |
| 6,178,355 B1 | * | 1/2001 | Williams et al. ............... 607/122 |
| 6,381,500 B1 | * | 4/2002 | Fischer, Sr. .................... 607/127 |
| 2002/0038135 A1 | | 3/2002 | Connelly et al. ................. 607/32 |
| 2003/0040787 A1 | * | 2/2003 | Flynn et al. .................... 607/122 |
| 2003/0074040 A1 | * | 4/2003 | Florio et al. ................... 607/119 |
| 2003/0144719 A1 | | 7/2003 | Zeijlemaker .................. 607/122 |
| 2003/0144720 A1 | | 7/2003 | Villaseca et al. |
| 2003/0144721 A1 | | 7/2003 | Villaseca et al. |
| 2004/0215299 A1 | | 10/2004 | Zhao et al. ..................... 607/116 |

FOREIGN PATENT DOCUMENTS

WO    WO 00/27279 A1    5/2000    ............... A61B 5/04
WO    WO 03089045 A2 *    10/2003

OTHER PUBLICATIONS

PCT Search Report, PCT/US2006/011241, 2007, 4 pages.

* cited by examiner

*Primary Examiner* — Tammie K Heller
(74) *Attorney, Agent, or Firm* — Michael J. Ostrom; Stephen W. Bauer

(57) ABSTRACT

A multi-conductor medical electrical lead comprises a connector located at a proximal end of the lead, one or more electrodes located at a distal end of the lead and a co-radial multi-conductor coil connecting the connector with the electrode(s), wherein the coil has a lead body region with co-radially wound conductors and has an inductance greater than or equal to approximately 1.5 μH.

19 Claims, 6 Drawing Sheets

MEDICAL ELECTRICAL LEAD WITH CO-RADIAL MULTI-CONDUCTOR COIL

FIELD OF THE INVENTION

The present invention relates generally to implantable medical device (IMD) leads for delivering active electrodes to various places in a human body, such as the heart. In particular, the present invention relates to leads capable of operating in radio frequency (RF) fields generated by magnetic resonance imaging (MRI).

BACKGROUND OF THE INVENTION

Endocardial leads, used for cardiac pacing, cardioversion and monitoring, are placed through a transvenous route to position one or more sensing and/or stimulation electrodes in a desired location within a heart chamber or interconnecting vasculature. Routing an endocardial lead along a desired path to a target implant site can be difficult and is dependant upon the physical characteristics of the lead. One type of lead includes a plurality of individually insulated wires or filars formed in a coil that extends from the proximal to the distal end of the lead. Each electrode carried by the lead is electrically connected to one of the wires.

Advancements in medical technology have led to the use of devices for imaging and for therapy that involve exposing a patient to energy fields that may be disruptive to implantable medical devices. For example, magnetic resonance imaging generates cross-sectional images of a human body using nuclear magnetic resonance (NMR). The MRI process begins with positioning a body to be imaged in a strong, uniform magnetic field, which polarizes the nuclear magnetic moments of protons within hydrogen molecules in the body by forcing their spins into one of two possible orientations. Then an appropriately polarized radio-frequency field, applied at resonant frequency, forces spin transitions between these orientations. The spin transitions create a signal, an NMR phenomenon, which can be detected by a receiving coil.

Traditionally, the use of magnetic resonance imaging has been discouraged for patients with implantable medical devices because the energy fields generated during operation of the MRI may interfere with or affect the performance of the IMD. Particularly, RF fields generated by magnetic resonance imaging might cause conductors used in the leads of an IMD to heat up, causing local burns in the body.

The tendency of lead electrodes to heat up when placed in a RF field is related to the inductance of the lead coil, because wound conductors are particularly susceptible to excitation from RF fields. Generally, it is desirable for a lead coil to have increased inductance in order to minimize effects from RF fields generated during magnetic resonance imaging.

Therefore, it is desirable to have an IMD lead that is capable of carrying multiple electrodes, has good handling and endo-vascular mobility, is small in diameter (i.e. less than 7 French (~0.9185 inches)) and can be used in an MRI environment.

BRIEF SUMMARY OF THE INVENTION

The present invention comprises a multi-conductor medical electrical lead comprising a connector located at a proximal end of the lead, one or more electrodes located at a distal end of the lead and a co-radial multi-conductor coil connecting the connector with the electrodes, wherein the coil includes a plurality of co-radially wound conductors having an inductance greater than or equal to 1.5 µH.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE INVENTION

Figure 1:
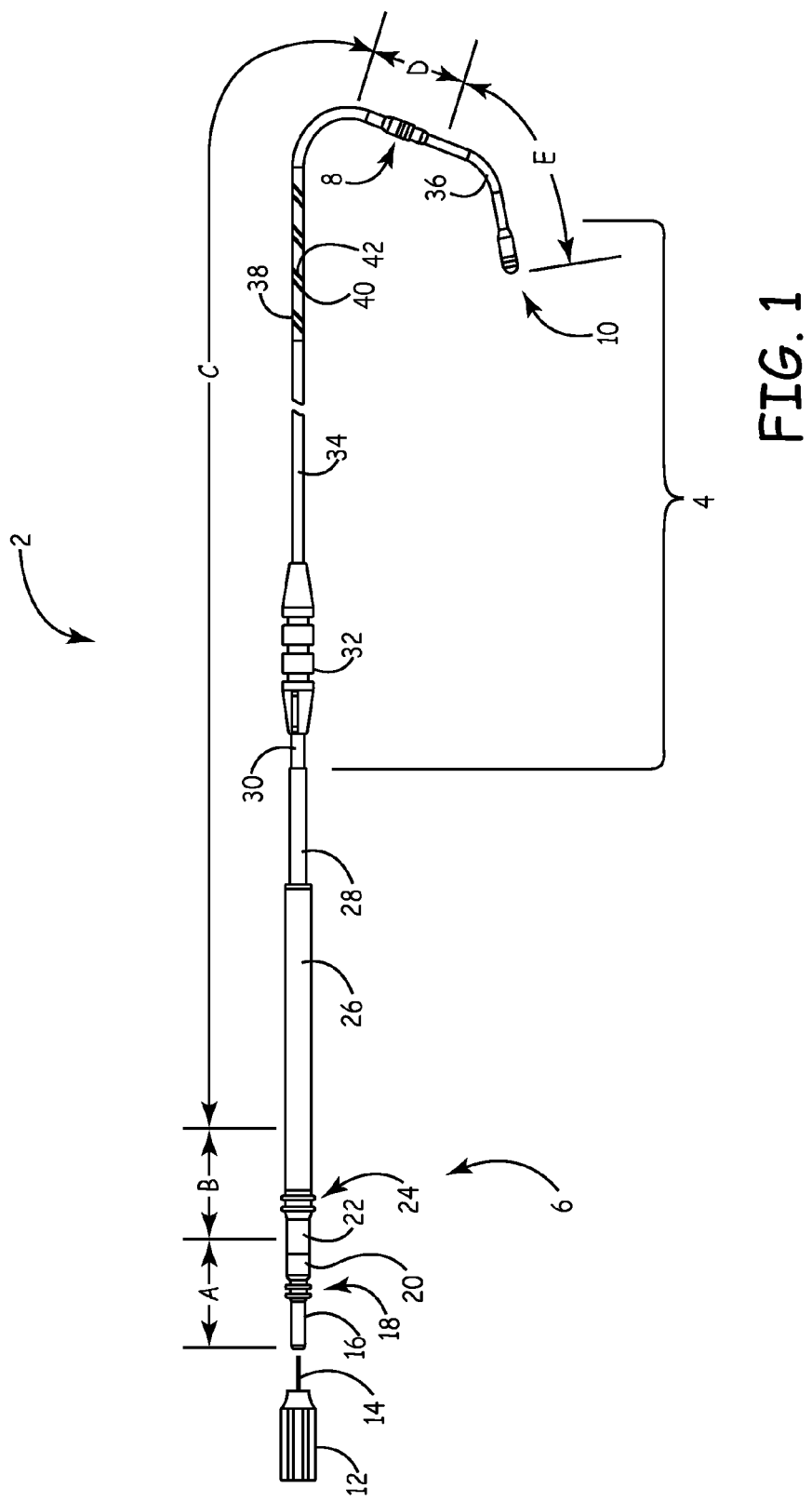
FIG. 1 shows a left ventricular lead according to the present invention.

FIG. 1 shows a left ventricle (LV) lead according to the present invention. Lead 2 includes lead body 4, connector assembly 6, LV pace/sense ring electrode assembly 8 and LV pace/sense tip electrode assembly 10. Knob 12 and stylet 14 are also shown. Stylet 14 is employed to straighten lead body 4 during insertion of lead 2 into the coronary sinus and great cardiac vein.

Connector assembly 6 is located at the proximal end of lead 2, and is comprised of connector pin 16, proximal sealing rings 18, coupler 20, connector ring 22, distal sealing rings 24, connector sleeve 26 and strain relief tubing 28. Lead body 4 extends distally from connector assembly 6 and is comprised of first sheathing 30, anchor sleeve 32, second sheathing 34, third sheathing 36 and coil assembly 38 (which is shown in a portion of lead body 4 where sheathing 34 is broken away.) Coil assembly 38 formed by insulated conductors 40 and 42 which are wound together. Conductor 40 connects ring electrode assembly 8 with connector ring 22 and conductor 42 connects tip electrode assembly 10 with connector pin 16.

Connector pin 16 provides an access point for stylet 14 (or a guide wire) to enter lead 2. Connector pin 16 also provides an electrical connection between conductor 42 and the IMD circuitry when connector assembly 6 is inserted into a connection bore of an IMD. This, in turn, provides an electrical connection between tip electrode assembly 10 and the IMD circuitry. Proximal sealing rings 18 prevent fluids from the body in which lead 2 is implanted from entering the IMD. Coupler 20 connects connector pin 16 and proximal sealing rings 18 with connector ring 22, distal sealing rings 24 and connector sleeve 26. Connector ring 22 provides an electrical connection between conductor 40 and the IMD circuitry when connector assembly 6 is inserted into a connection bore of an IMD. This, in turn, provides an electrical connection between ring electrode assembly 8 and the IMD circuitry.

Distal sealing rings 24 prevent fluids from the body in which lead 2 is implanted from entering the IMD. Connector sleeve 26 provides a rigid housing for the internal components of connector assembly 6. Strain relief tubing 28 provides a flexible transition region between lead body 4 and connector assembly 6 to prevent kinking or straining of lead body 4. Sheathings 30, 34 and 36 provide a protective barrier between coil assembly 38 and the body in which lead 2 is implanted. Anchor sleeve 32 is used to secure lead 2 in place once the desired positioning of lead body 4 has been achieved.

Lead 2 includes five regions A-E that represent different winding characteristics of coil assembly 38. Region A represents the connector pin 16 region, region B represents the connector ring 22 region, region C represents the lead body 4 region, region D represents the ring electrode assembly 8 region, and region E represents the tip electrode assembly 10 region.

Figure 2A:
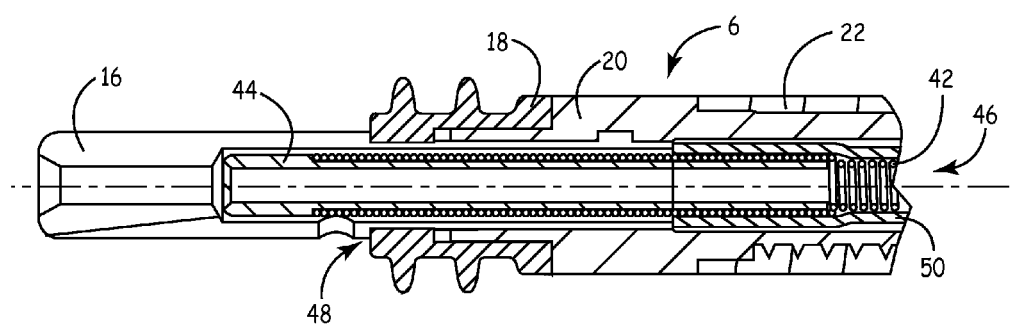
FIG. 2A shows a cross sectional view of a connector pin region of the lead of FIG. 1.

FIG. 2A shows a cross sectional view of connector pin 16 of connector 6 as used in lead 2 of FIG. 1. FIG. 2A is also representative of region A of FIG. 1. Conductor 42 is wound around crimp core 44 in order to provide a mechanical connection between conductor 42 and connector 6. Conductor 42 continues to be wound as coil 46A as it comes off of crimp core 44. Crimp core 44 fits inside connector pin 16, which provides an access point for stylet 14. Crimp 48 secures conductor 42 to crimp core 44 and connector pin 16. The crimping action of crimp 48 deforms conductor 42 such that the insulation surrounding conductor 42 is spread apart, thereby providing an electrical connection between connector pin 16 and conductor 42. Connector pin 16 provides an electrical connection between conductor 42 and the IMD circuitry. Core sleeve 50 connects crimp core 44 used with conductor 42 with the crimp core used with conductor 40.

Figure 2B:
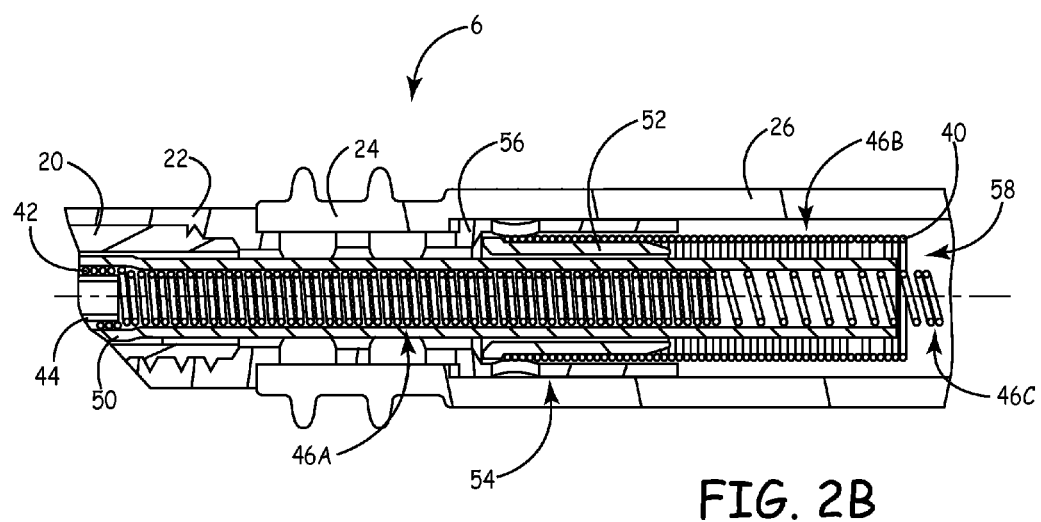
FIG. 2B shows a cross sectional view of a connector ring region of the lead of FIG. 1.

FIG. 2B shows a cross sectional view of connector ring 22 of connector 6 as used in lead 2 of FIG. 1. FIG. 2B is also representative of region B of FIG. 1. Conductor 40 is wound around crimp core 52 in order to provide a mechanical connection between conductor 40 and connector 6. Conductor 40 continues to be wound as coil 46B as it comes off of core 52. Core 52 fits inside crimp sleeve 56 and around core sleeve 50. Crimp sleeve 56 is crimped to form crimp 54. The crimping action of crimp 54 deforms conductor 40 such that the insulation surrounding conductor 40 is spread apart, thereby providing an electrical connection between conductor 40 and crimp sleeve 56. Crimp sleeve 56 is integral with connector ring 22 which provides an electrical connection between conductor 40 and the IMD circuitry. Core sleeve 52 connects crimp core 44 and conductor 42 with crimp core 52 and conductor 40, thus coaxially aligning coil 46B with coil 46A. At position 58, the pitch of coil 46A is increased and conductor 40 of coil 46B is wound to have outside diameter OD and is co-radially wound with conductor 42 to form coil 46C. Coil 46C is representative of the coil in region C.

Figure 2C:
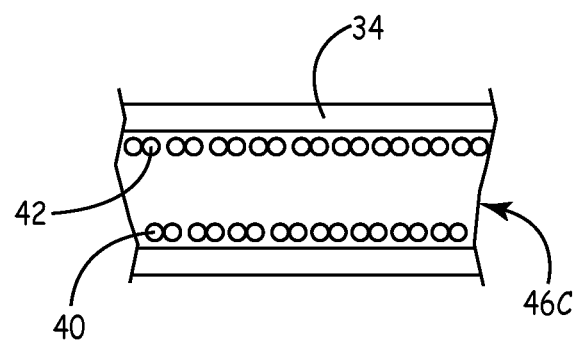
FIG. 2C shows a cross sectional view of a lead body region of the lead of FIG. 1.

FIG. 2C shows a cross sectional view of lead body 4 region as used in lead 2 of FIG. 1. Coil 46C is wrapped by sheathing 34, isolating it from the body in which it is implanted. Coil 46C is comprised of conductors 40 and 42, which are co-radially wound such that they have the same outside diameter. Each conductor is individually insulated to prevent electrical connection between the conductors.

Figure 2D:
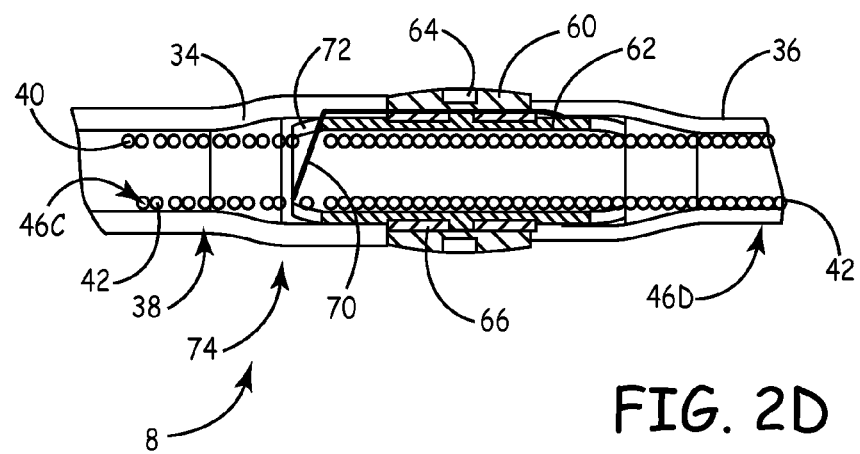
FIG. 2D shows a cross sectional view of a ring electrode region of the lead of FIG. 1.

FIG. 2D shows a cross sectional view of ring electrode assembly 8 as used in lead 2 of FIG. 1. FIG. 2D is also representative of region D from FIG. 1. Ring electrode assembly 8 includes ring electrode 60, electrode core 62, Monolithic Controlled Release Device (MCRD) 64 and titanium ring 66. MCRD 64 time releases steroids into the body in which lead 2 is implanted in order to reduce inflammation of tissue caused by the presence of lead 2 in the body.

As coil 46C approaches electrode 60, conductors 40 and 42 enter electrode core 62, where, at position 74, conductor 40 is peeled up and away from coil 46C. Peeled up portion 70 of conductor 40 passes through opening 72 in electrode core 62 and is laid up against the outer surface of titanium ring 66. Electrode 60 is force fit around titanium ring 66 while peeled up portion 70 is positioned between them. The inside diameter of electrode 60 is large enough to fit around the outside diameter of titanium ring 66 and peeled up portion 70 of conductor 40. The diameter is such that when electrode 60 is fit around titanium ring 66 and peeled up portion 70, the edge of electrode 60 along the inside diameter of electrode 60 strips away any insulating material around peeled up portion 70 of conductor 40, producing an electrical connection between conductor 40 and electrode 60. Titanium ring 66 provides a rigid foundation which conductor 40 can be pressed against during the force fitting procedure. Sheathing 34 continues around electrode core 62 and peeled up portion 70 and extends all the way so as to butt up against a proximal end of electrode 60. Conductor 42 and sheathing 36 continue to extend toward tip electrode assembly 10 (not shown), passing through electrode core 62 as coil 46D.

Figure 2E:
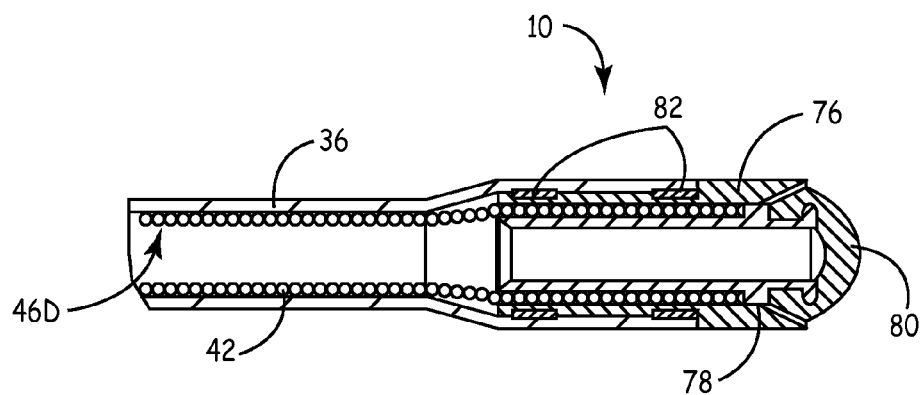
FIG. 2E shows a cross sectional view of a tip electrode region of the lead of FIG. 1.

FIG. 2E shows a cross sectional view of tip electrode assembly 10 used in lead 2 of FIG. 1. FIG. 2E is also representative of region E from FIG. 1. Distal electrode assembly 10 is comprised of tip electrode 76, electrode core 78 and tip seal 80. Tip electrode 76 further comprises port holes 82.

Conductor 42 of coil 46D is wrapped around electrode core 78. Electrode 76 is force fit around electrode core 78 while conductor 42 is positioned between them. The inside diameter of electrode 76 is large enough to fit around the outside diameter of electrode core 78 and conductor 42. The diameter is such that when electrode 76 is fit around electrode core 78 and conductor 42, the edge of electrode 76 along the inside diameter of electrode 76 strips away any insulating material around conductor 42, producing an electrical connection between conductor 42 and electrode 76. Sheathing 36 continues around electrode core 78 and conductor 42 and extends all the way to tip electrode 76. Tip seal 80 is insert molded onto electrode core 78 prior to assembly into conductor 42 and is sealed with a silicone adhesive at the time of assembly. Port holes 82 are also filled with a silicone adhesive, and polyurethane adhesive is used to bond sheathing 36 with tip electrode 76.

In one example, conductors 40 and 42 are made of silver core MP35N wires, sheathings 30, 34 and 36 are made from polyurethane, electrode core 62 is made of polyurethane and electrode 60 has a TiN coating.

It is particularly advantageous to have the crimping action and stripping action of the force fitting to connect conductors 40 and 42 with crimp cores 44 and 52 and titanium ring 66 and electrode core 78 when very thin coatings of SI polyimide are used to insulate conductors 40 and 42 because it eliminates the need for an additional ablation step to remove the insulation. Having a thin insulating layer assists in keeping the overall dimensions of coil assembly 38 (and therefore lead 2) to a minimum. This helps in designing leads with desirable MRI compatibility characteristics and handling and endovascular mobility.

The handling characteristics of lead 2 can be further controlled utilizing resiliency properties of sheathings 30, 34 and 36. Leads having smaller diameters are more readily insertable into the body, but they can become more difficult for a doctor to control during insertion if they are too flexible, especially in catheter delivered leads. Therefore, stiffer sheathing can be used when more rigid leads are desired. Thus, doctors have the benefit of small diameter leads with optimized handling characteristics.

For MRI compatible lead designs, the conductor coil inductance is one factor that can impact the final lead performance in terms of reduced heating at the distal end electrodes. An inductance value greater than or equal to 1.5 µH has been shown to be effective at minimizing heating at the distal end electrodes. Thin SI polyimide insulation layers, as disclosed in U.S. Application No. 2004/0215299, allow co-radial multi-conductor coil assemblies to be wound to have the characteristics which give it a total inductance greater than or equal to 1.5 µH.

As indicated above, it is desirable for conductor coil assemblies to have a total inductance greater than or equal to 1.5 µH. The following characteristics are determinative of the inductance of a coil: the diameter of each wire conductor, the pitch of the coil, the inside diameter of the coil excluding insulation and the length of the coil. Additionally, the characteristics of a conductor coil are limited by the design requirements for the specific application in which it will be used. It is generally desirable that the coil have an inner diameter less than or equal to 0.022 inches or (~0.0559 cm); this allows for safe passage of a guide wire or stylet and also helps maintain a smaller outer diameter lead body. Yet another limitation on the characteristics of a co-radial multi-conductor coil is the need to electrically insulate each conductor in the coil. Individually insulating each conductor increases the pitch of the coil as compared to a coil with non-insulated conductors.

Figure 3:
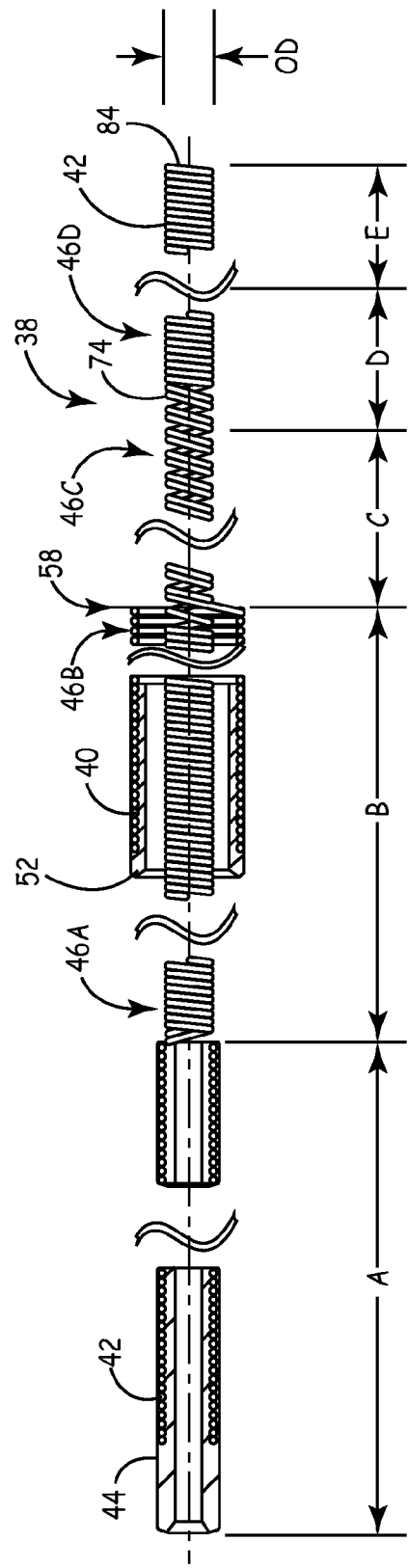
FIG. 3 shows a co-radial multi-conductor coil assembly according to the present invention as used in the lead shown in FIG. 1.

FIG. 3 shows co-radial multi-conductor coil assembly 38 of lead 2 shown in FIG. 1. Coil assembly 38 is wound to have a total inductance greater than 1.5 µH. Regions A-E are shown on coil assembly 38 that correspond to regions A-E of lead 2 in FIG. 1.

Coil assembly 38 comprises two conductors 40 and 42, and crimp cores 44 and 52, which are used for connecting conductors 40 and 42 to IS-1 connector 6. Conductor 42 is wound around crimp core 44. As conductor 42 comes off crimp core 44, it continues to be tight wound as coil 46A and has outside diameter OD. Crimp core 52 is concentrically located around coil 46A at a distance determined by the IS-1 connector 6. Conductor 40 is wound around crimp core 52. As conductor 40 comes off of crimp core 52, it continues to be tight wound as coil 46B. At position 58, the pitch of coil 46A is increased and conductor 40 of coil 46B is wound to have outside diameter OD and is co-radially wound with conductor 42 to form coil 46C. Coil 46C is representative of the coil in region C.

At position 74, conductor 40 is peeled up from coil 46D where it terminates and is connected to ring electrode 60 of ring electrode assembly 8 of FIG. 1. At position 74, the pitch of conductor 42 is adjusted to form coil 46D. At position 84, conductor 42 terminates and is connected to tip electrode 76 from tip electrode assembly 10 of FIG. 1.

For each region in a conductor coil assembly having different coil characteristics, there is an associated inductance. Thus, the inductance, $L_{total}$, of coil assembly 38, comprising coils 46A, 46B, 46C and 46D, equals the sum of the inductances of each coil, and is approximated by the following equation, $$L_{total} = L_{46A} + L_{46B} + L_{46C} + L_{46D} \quad \text{[Equation 1]}$$

where each inductance $L_{46A}$, $L_{46B}$, $L_{46C}$, and $L_{46D}$ is a function of the number of turns of the coil in that region, the length of the coil in that region, the area inside the coil in that region, the number of conductors, the permeability of the conductors, and the pitch of the coil in that region, where pitch is equal to the number of turns in a coil region divided by the coil length.

Thus, by controlling the inductance of each portion of coil assembly 38, it is possible to have a co-radial multi-conductor lead that is capable of connecting multiple electrodes to an IS-1 connector and is also MRI compatible. This is made possible by the single conductor coil—to dual coaxial coil—to co-radial coil—to single conductor coil arrangement of coil assembly 38. Coil assembly 38 starts out as single conductor coil 46A which is used to connect conductor 42 with connector pin 16 for the IS-1 connector configuration. Then, coil 46A is coaxially wound with single conductor coil 46B which is used to connect conductor 40 with connector ring 22 for the IS-1 connector configuration. Next, coils 46A and 46B are co-radially wound to form coil 46C which provides a narrow diameter coil for forming small diameter lead body 4. Finally, conductor 40 is peeled away from coil 46C for connecting to ring electrode 60, leaving conductor 42 to form coil 46D for connecting to tip electrode 76.

Co-radial multi-conductor leads with an outside diameter of, but not limited to, 4 French (~0.0525 inch or 0.1332 cm) and having a coil assembly with an overall inductance of at least 1.5 µH can be created with as many as six conductors in order to have up to six electrodes. The necessary coil parameters for these leads are contained in Table 1 with approximate values.

TABLE 1

| # of conductors | Wire OD (inches) [mm] | Coil OD w/o insulation (inches) [mm] | Coil ID w/ insulation (inches) [mm] | Filar Insulation Thickness (inches) [mm] | Coil Resistance (Ω/circuit) | Coil Pitch (inches) [mm] | Coil Length (inches) [mm] | Coil Inductance (µH) worst case | Electrode Surface Area (mm²) |
|---|---|---|---|---|---|---|---|---|---|
| 2 | .004 [.102] | ≥0.030 [.762] | ≥0.021 [.5334] | ≤.0005 [.0127] | <200 | ≤0.015 [.381] | ≥30 [762] | 1.56 | ≥2.2 |
| 3 | .0035 [.0889] | ≥0.030 [.762] | ≥0.021 [.5334] | ≤.0005 [.0127] | <200 | ≤0.015 [.381] | ≥30 [762] | 1.51 | ≥2.2 |
| 4 | .003 [.0762] | ≥0.030 [.762] | ≥0.021 [.5334] | ≤.0005 [.0127] | <200 | ≤0.016 [.4064] | ≥30 [762] | 1.50 | ≥2.2 |
| 6 | .0025 [.0635] | ≥0.034 [.8636] | ≥0.025 [.635] | ≤.00025 [.00635] | <200 | ≤0.019 [.4826] | ≥30 [762] | 1.53 | ≥2.2 |

Leads with additional conductors can also be produced, but are limited by the physical properties of the conductors, such as diameter and conductivity. Larger diameter leads can also be created for use in left ventricle applications. Therefore, leads having a coil assembly inductance of at least 1.50 µH and having the required outside diameter for various applications, can be produced using SI-polyimide insulation to obtain the required coil parameters. In addition to inductance values as the sole determinant of MRI compatibility, the overall length of the lead should be tuned to optimize the lead performance (i.e. reduce the potential for electrode heating) in the high frequency RF field of an MR scan. The optimal length is specific to an individual lead design and can be determined using modeling and experimental techniques.

Figure 4:
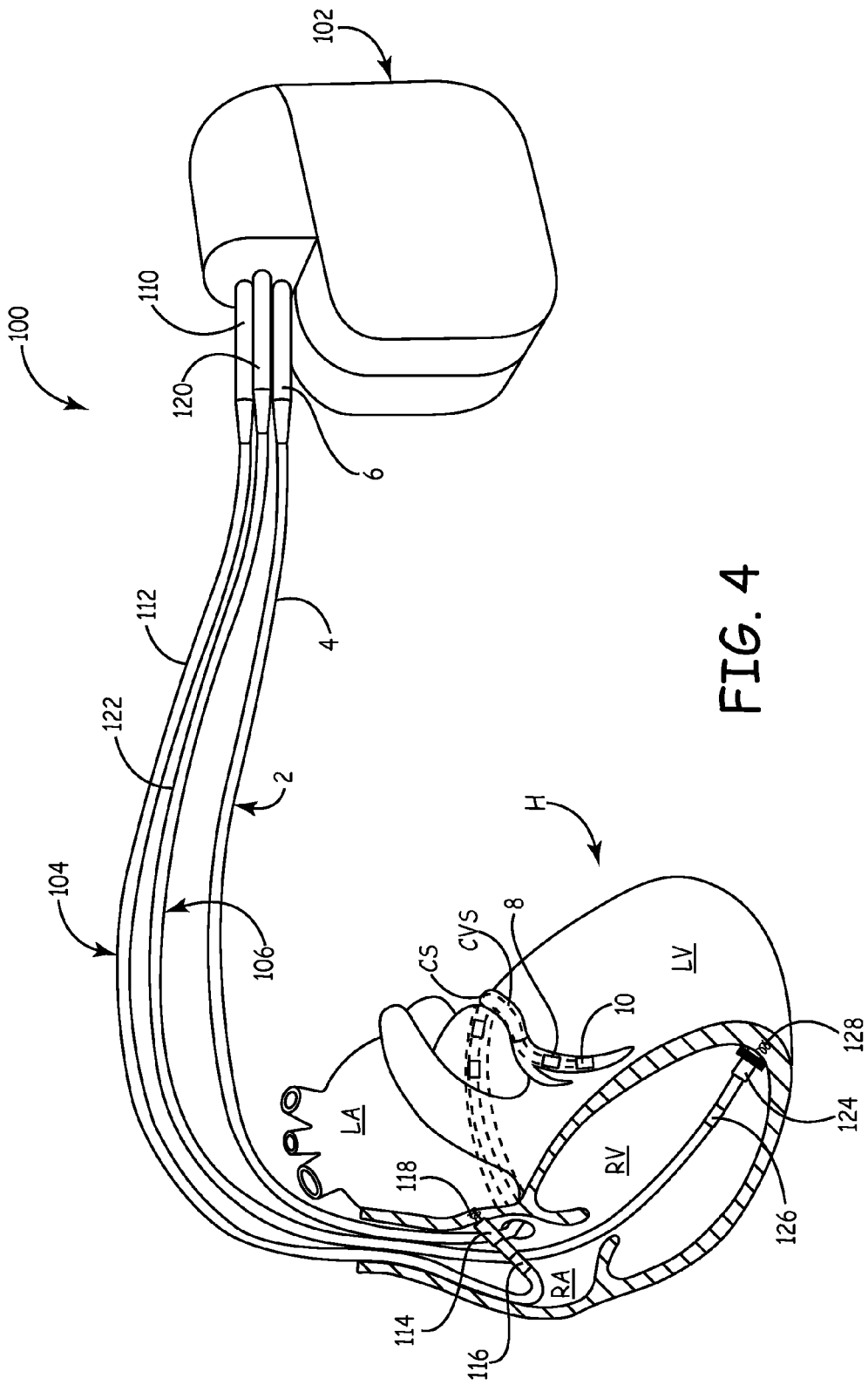
FIG. 4 shows an implantable medical device including the lead of the present invention.

FIG. 4 shows lead 2 in use as part of a cardiac resynchronization therapy (CRT) system 100, which is exemplary of implantable systems in which the present invention can be utilized. Heart H is shown in a partially cutaway view illustrating right atrium RA, left atrium LA, right ventricle RV, left ventricle LV, coronary sinus CS, and coronary venous system CVS. CRT system 100 includes implantable pulse generator (IPG) 102, right atrial (RA) lead 104, right ventricular (RV) lead 106 and left ventricular (LV) lead 2. Connector 6, ring electrode assembly 8 and tip electrode assembly 10 are also shown as part of left ventricle lead 2. RA lead 104 has connector 110 at its proximal end, lead body 112, and tip electrode 114, ring electrode 116 and fixation device 118 at its distal end. RV lead 106 has connector 120 at its proximal end, lead body 122, and tip electrode 124, ring electrode 126 and fixation device 128 at its distal end. Leads 90, 92 and 94 can be constructed according to the present invention.

Multi-conductor co-radial leads can be produced having electrodes from as low as one up to as many as eight or more. Multiplexing circuitry within the IPG can be used to select the particular electrode(s) that are active at any given time. In another example, Brady pacing leads, wherein two uninsulated co-radially wound leads connect a single electrode to an IMD, can be produced according to the present invention. These Brady pacing leads may have diameters up to approximately 6 or 7 French (~0.07866 or 0.09185 inches). Leads made according to the present invention can be used in various IMD systems for a variety of applications. For example, leads may be positioned adjacent to or within the spinal column, myocardial tissue, brain tissue or smooth muscle tissue.

Although the present invention has been described with reference to preferred embodiments, workers skilled in the art will recognize that changes may be made in form and detail without departing from the spirit and scope of the invention. Medical electrical leads with co-radial conductor coils can be produced having various parameters for use in various applications.

What is claimed is:

1. A multi-conductor medical electrical lead comprising:
   a connector located at a proximal end of the lead;
   at least one electrode located at a distal end of the lead;
   a co-radial multi-conductor coil extending from the proximal end of the lead to the at least one electrode and connecting the connector with the electrode, wherein the coil includes a plurality of conductors co-radially wound such that the coil has an inductance greater than or equal to approximately 1.5 µH, wherein all regions of the coil extending from the proximal end of the lead to the at least one electrode contribute to the inductance greater than or equal to approximately 1.5 µH to reduce excitation along the coil extending from the proximal end of the lead to the at least one electrode by RF fields generated during magnetic resonance imaging; and
   sheathing along and surrounding the coil extending from the proximal end of the lead to the at least one electrode to provide a protective barrier between the coil and the body when the lead is implanted therein, wherein the sheathing has a thickness less than 0.009 inches, and further wherein the lead is configured such that the sheathing from the proximal end of the lead to the at least one electrode contacts the body when implanted therein.

2. The multi-conductor lead of claim 1 wherein each conductor includes a SI-polyimide insulating layer.

3. The multi-conductor lead of claim 2 wherein the SI-polyimide insulating layer includes a thickness less than or equal to approximately 0.0005 inches (0.00127 cm).

4. The multi-conductor lead of claim 1 wherein the plurality of conductors include two conductors having a diameter less than or equal to approximately 0.004 inches (0.01016 cm).

5. The multi-conductor lead of claim 1 wherein the coil includes an outside diameter greater than or equal to approximately 0.030 inches (0.0762 cm).

6. The multi-conductor lead of claim 1 wherein the coil includes a pitch less than or equal to approximately 0.019 inches (0.04829 cm).

7. The multi-conductor lead of claim 1 wherein a length of the lead is greater than or equal to approximately 30 inches (76.2 cm).

8. The multi-conductor lead of claim 1 wherein the electrode includes a surface area greater than or equal to approximately 2.2 square millimeters.

9. The multi-conductor lead of claim 1 wherein the lead includes a tip electrode and a ring electrode, wherein a first conductor is peeled away from the coil and connected to the ring electrode, and wherein a second conductor is connected to the tip electrode.

10. The multi-conductor lead of claim 1 wherein the lead includes an outside diameter of approximately 4 French.

11. The multi-conductor lead of claim 1 wherein the coil comprises:
   a first single conductor coil portion comprised of a first conductor;
   a second single conductor coil portion comprised of a second conductor, coaxially and concentrically located with respect to the first single conductor coil portion;
   a co-radial coil portion, wherein the first conductor of the first single conductor coil portion and the second conductor of the second single conductor coil portion are co-radially wound together to have the same diameter; and
   a third single conductor coil portion comprised of the first conductor.

12. The lead of claim 1 wherein one of the conductors includes connection to one of the electrodes by a force fit, wherein the conductor includes terminal winding around an electrode core and the electrode is force fit around the electrode core and the conductor, deforming a portion of an insulating layer around the conductor and producing an electrical connection between the conductor and the electrode.

13. An implantable medical device comprising:
   an implantable pulse generator;
   an electrical lead including a connector at a proximal end connected to the implantable pulse generator, an electrode at a distal end, and a co-radial, multi-conductor coil extending from the proximal end of the lead to the electrode and connecting the electrode and the connector, wherein the coil has an inductance of at least approximately 1.5 µH, wherein all regions of the coil extending from the proximal end of the lead to the electrode contribute to the inductance greater than or equal to approximately 1.5 µH to reduce excitation along the coil extending from the proximal end of the lead to the electrode by RF fields generated during magnetic resonance imaging; and
   sheathing along and surrounding the coil extending from the proximal end of the lead to the electrode to provide a protective barrier between the coil and the body when the lead is implanted therein, wherein the sheathing has a thickness less than 0.009 inches, and further wherein the lead is configured such that the sheathing from the proximal end of the lead to the electrode contacts the body when implanted therein.

14. A multi-conductor medical electrical lead for an implantable medical device, comprising:
   a connector located at a proximal end of the lead;
   at least one electrode located at a distal end of the lead;
   a multi-conductor coil extending from the proximal end of the lead to the at least one electrode, wherein the multi-conductor coil connects the connector with the at least one electrode, wherein the multi-conductor coil comprises a plurality of conductors co-radially wound such that the multi-conductor coil has an inductance greater than or equal to approximately 1.5 µH, wherein all regions of the multi-conductor coil extending from the proximal end of the lead to the at least one electrode contribute to the inductance greater than or equal to approximately 1.5 µH; and
   sheathing along and surrounding the multi-conductor coil extending from the proximal end of the lead to the at least one electrode to provide a protective barrier between the multi-conductor coil and the body when the lead is implanted therein, wherein the sheathing has a thickness less than 0.009 inches, and further wherein the lead is configured such that the sheathing from the proximal end of the lead to the at least one electrode contacts the body when implanted therein.

15. The multi-conductor lead of claim 14 wherein the plurality of conductors comprises two conductors having a diameter less than or equal to approximately 0.004 inches (0.01016 cm), wherein each conductor of the plurality of conductors comprises a SI-polyimide insulating layer, and further wherein the SI-polyimide insulating layer includes a thickness less than or equal to approximately 0.0005 inches (0.00127 cm).

16. The multi-conductor lead of claim 14 wherein the multi-conductor coil includes an outside diameter greater than or equal to approximately 0.030 inches (0.0762 cm).

17. The multi-conductor lead of claim 14 wherein the multi-conductor coil includes a pitch less than or equal to approximately 0.019 inches (0.04829 cm).

18. The multi-conductor lead of claim 14 wherein the lead includes an outside diameter of approximately 4 French.

19. The multi-conductor lead of claim 14 wherein the multi-conductor coil comprises:
   a first single conductor coil portion comprising a first conductor;
   a second single conductor coil portion comprising a second conductor, coaxially and concentrically located with respect to the first single conductor coil portion;
   a co-radial coil portion, wherein the first conductor of the first single conductor coil portion and the second conductor of the second single conductor coil portion are co-radially wound together to have the same diameter; and
   a third single conductor coil portion comprising the first conductor, wherein the sheathing covers the coil portions of the lead extending from the proximal end of the lead to the at least one electrode.

* * * * *